US009622917B2

(12) United States Patent
Takeuchi et al.

(10) Patent No.: US 9,622,917 B2
(45) Date of Patent: Apr. 18, 2017

(54) APPARATUS FOR MANUFACTURING ABSORBENT ARTICLES AND METHOD FOR MANUFACTURING ABSORBENT ARTICLES

(71) Applicant: UNICHARM CORPORATION, Shikokuchuo-shi, Ehime (JP)

(72) Inventors: Kenji Takeuchi, Kanonji (JP); Taizo Horiwaki, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 115 days.

(21) Appl. No.: 14/403,483

(22) PCT Filed: May 31, 2013

(86) PCT No.: PCT/JP2013/065174
§ 371 (c)(1),
(2) Date: Nov. 24, 2014

(87) PCT Pub. No.: WO2013/180261
PCT Pub. Date: Dec. 5, 2013

(65) Prior Publication Data
US 2015/0164698 A1    Jun. 18, 2015

(30) Foreign Application Priority Data

May 31, 2012    (JP) ................................. 2012-124892

(51) Int. Cl.
*A61F 13/15*    (2006.01)
*B32B 37/20*    (2006.01)
(Continued)

(52) U.S. Cl.
CPC .. *A61F 13/15601* (2013.01); *A61F 13/15609* (2013.01); *A61F 13/49017* (2013.01);
(Continued)

(58) Field of Classification Search
None
See application file for complete search history.

(56) References Cited

U.S. PATENT DOCUMENTS 8,944,129 B2 *  2/2015  Yamamoto ........ A61F 13/15609
                                              156/440
2010/0175807 A1    7/2010  Yamamoto

FOREIGN PATENT DOCUMENTS

EP    2486902 A1    8/2012
JP    4-317650 A    11/1992
(Continued)

OTHER PUBLICATIONS

Office Action mailed Oct. 6, 2015, corresponding to Japanese Patent Application No. 2012-124892.
(Continued)

*Primary Examiner* — Linda L Gray
(74) *Attorney, Agent, or Firm* — Hauptman Ham, LLP

(57) ABSTRACT

An apparatus for manufacturing absorbent articles includes: a swinging mechanism that feeds an elastic member while swinging the elastic member along a cross direction crossing a conveyance direction of a sheet-shaped continuum constituting an absorbent article, and that disposes a part of the elastic member on the continuum; a guiding member that conveys the elastic member; a cutting mechanism that cuts the elastic member; a joining mechanism that conveys the elastic member and the continuum that are supplied from the guiding mechanism to be taken along an outer periphery of the joining mechanism; and a sheet supply mechanism that supplies a sheet member onto an end portion in the cross direction of the continuum. A tangential direction of a deviation point at which the continuum is spaced from the guiding mechanism and a tangential direction of an arrival
(Continued)

point at which the continuum reaches the joining mechanism are coincident with each other.

4 Claims, 8 Drawing Sheets

(51) Int. Cl.
    *B32B 38/04*     (2006.01)
    *A61F 13/49*     (2006.01)
    *B32B 37/00*     (2006.01)
    *B32B 37/18*     (2006.01)
    *B32B 38/00*     (2006.01)
    *B32B 37/02*     (2006.01)
    *B32B 37/14*     (2006.01)
    *B32B 37/16*     (2006.01)

(52) U.S. Cl.
    CPC .......... *B32B 37/0046* (2013.01); *B32B 37/18* (2013.01); *B32B 38/0004* (2013.01); *B32B 38/0012* (2013.01); *A61F 13/15699* (2013.01); *A61F 13/15723* (2013.01); *A61F 13/15764* (2013.01); *A61F 2013/49038* (2013.01); *B32B 37/02* (2013.01); *B32B 37/144* (2013.01); *B32B 37/16* (2013.01); *B32B 2555/02* (2013.01); *Y10T 156/1026* (2015.01); *Y10T 156/1062* (2015.01); *Y10T 156/125* (2015.01); *Y10T 156/1322* (2015.01)

(56) References Cited

FOREIGN PATENT DOCUMENTS

| | | |
|---|---|---|
| JP | 2003-339769 A | 12/2003 |
| JP | 2011-156123 A | 8/2011 |
| WO | 2010/055910 A1 | 5/2010 |
| WO | 2010/071069 A1 | 6/2010 |
| WO | 2010/126415 A1 | 11/2010 |

OTHER PUBLICATIONS

Extended European Search Report dated Oct. 21, 2015, corresponding to European Patent Application No. 13798142.9.
International Search Report mailed Aug. 20, 2013 in International Application No. PCT/JP2013/065174 filed May 31, 2013.
Office Action in GCC Application No. 2013-24550, dated Aug. 4, 2016.

* cited by examiner

The present application is a National Phase of International Application Number PCT/JP2013/065174, filed May 31, 2013, which claims priority to Japanese Application Number 2012-124892, filed May 31, 2012.

APPARATUS FOR MANUFACTURING ABSORBENT ARTICLES AND METHOD FOR MANUFACTURING ABSORBENT ARTICLES

RELATED APPLICATIONS

TECHNICAL FIELD

The present invention relates to an apparatus for manufacturing absorbent articles and a method for manufacturing absorbent articles, the apparatus and method disposing an elastic member on a sheet-shaped continuum constituting an absorbent article.

BACKGROUND ART

In an absorbent article such as a disposable diaper or disposable shorts, a structure to provide a so called leg gather is widely employed so as to fit to a leg-line portion corresponding to a leg of a wearer. In such absorbent article, a fitting to a wearer (in particular, a leg) can be ensured, since a leg gather expands and contracts in accordance of a shape of a leg-line portion or a movement of the wearer.

In general, as a method for manufacturing a leg gather according to a shape of leg-line portion, there is well known a method for disposing an elongated elastic member (for example, a fiber-shaped rubber) in an expanded state on a sheet-shaped continuum such as a web to be conveyed. Specifically, the elastic member can be disposed in a wavy shape having a predetermined amplitude on the continuum to be conveyed, by a swinging mechanism to feed the elastic member while swinging (reciprocally) along a cross direction crossing a conveyance direction of the continuum. The elastic member disposed in the wavy shape is adhered onto the continuum via an adhesive or the like, and the continuum thus adhered is cut in product size so that the shape of the elastic member fits to the shape of the leg-line portion of the wearer.

In addition, in disposable shorts or the like for incontinence at a light level, there is a need for a comfortable feeling of wearing of underwear or the like and thus it is preferable to have a further high feeling of fitting. Therefore, there is known a method for disposing a part of an elastic member that is to be disposed in a wavy shape by a swinging mechanism so as to deviate from a widthwise end portion of a continuum to the outside (for example, Patent Literature 1, pages 8 to 9, and FIG. 4). According to such a method, it becomes easy to dispose an elastic member in an entire region of a leg-line portion or to form the shape of the elastic member to further fit to the shape of the leg-line portion. It is to be noted that in this case, an elastic member that is not disposed on the continuum (an elastic member having deviates outboard of t the end of the continuum in widthwise direction) is cut and removed in the steps on a downstream side.

Incidentally, in recent years, in disposable diapers, there has been a so called three-piece disposable diaper to separately form a foreside region and a backside region, and joining the foreside region and the backside region with each other through an absorbent main body having an absorber (for example, refer to Patent Literature 2, FIGS. 2 to 4). When a leg-line elastic member such as a leg gather is disposed in a continuum constituting the foreside region, the step of disposing the elastic member in a continuum constituting the foreside region and the step of disposing the elastic member in a continuum constituting the backside region are provided.

CITATION LIST

Patent Literature

[PTL 1]
Japanese Unexamined Patent Application Publication No. H04-317650
[PTL 2]
Japanese Unexamined Patent Application Publication No. 2003-339769

SUMMARY OF INVENTION

However, the conventional manufacturing methods described above entail the following problems.

A manufacturing method described in Patent Literature 1 is to cut an elastic member deviating from a continuum to the outside. The cut elastic member separates from the continuum. On the other hand, an elastic member remaining on the continuum is disposed on the continuum in an expanded state in a longitudinal direction along edges of an absorber in the widthwise direction. A rigidity of the absorber is higher than a rigidity of a continuum constituting an exterior sheet or the like. Therefore, at a portion disposed along the absorber, a contraction due to a stress of the elastic member hardly occurs. However, an end portion of the continuum is comparatively distant from the absorber and a rigidity of the end portion is low, therefore, the contraction due to the stress of the elastic member easily occurs. For example, if a part of the continuum contracts, a position of the continuum relative to another member may be shifted in a next step or assembling in a twisted state may occur.

In addition, in a disposable diaper described in Patent Literature 2, if an attempt is made to dispose an elastic member in an entire region of a leg-line portion, an elastic member is disposed at a respective one of a foreside region continuum and a backside region continuum, and is cut in that state. Next, it is considered that an absorbent main body to an appropriate site is adhered so as to be across a cutting unit in the foreside and a cutting unit in the backside region.

However, in the foreside region continuum and the backside region continuum, an absorber with its comparatively high rigidity is not disposed and thus a contraction force due to a stress of the elastic member may increase. Therefore, in the manufacturing steps, a position between the foreside region or the backside region and the absorbent main body may be shifted.

Accordingly, the present invention has been made in view of such circumstance, and it is an object of the present invention to provide an apparatus for manufacturing absorbent articles and a method for manufacturing absorbent articles, which are capable of disposing an elastic member in an entire region of a leg-line portion while restraining a positional shift between the constituent members.

In order to resolve the above problem, the apparatus for manufacturing absorbent articles according to the present disclosure is summarized as the apparatus for manufacturing absorbent articles including: a swinging mechanism that feeds an elastic member while swinging the elastic member along a cross direction crossing a conveyance direction of a sheet-shaped continuum constituting an absorbent article, and that disposes a part of the elastic member on the continuum to which an adhesive is applied; a guiding member that conveys the elastic member and the continuum to be taken along an outer periphery of the guiding member with a guide mechanism shaft being a center of swivel rotation; an outside pressing mechanism that presses the elastic member disposed outer side in a cross direction than the continuum of the elastic member disposed in a predetermined wavy shape by the swinging mechanism; a cutting mechanism that cuts the elastic member conveyed by the guiding mechanism between the outside pressing mechanism and the continuum in the cross direction; a joining mechanism that conveys the elastic member and the continuum that are supplied from the guiding mechanism to be taken along an outer periphery of the joining mechanism with a joining mechanism shaft being a center of swivel rotation; and a sheet supply mechanism that supplies a sheet member onto an end portion in the cross direction of the continuum that is conveyed by the joining mechanism, wherein a tangential direction of a deviation point at which the continuum is spaced from the guiding mechanism and a tangential direction of an arrival point at which the continuum reaches the joining mechanism are coincident with each other.

The method for manufacturing absorbent articles according to the present disclosure is summarized as the method for manufacturing absorbent articles including: an elastic member disposition step of feeding an elastic member with the elastic member being swung along a cross direction crossing a conveyance direction of a sheet-shaped continuum constituting an absorbent article, and disposing a part of the elastic member on the continuum to which an adhesive is applied; a guiding step of conveying the elastic member and the continuum so as to be taken along an outer periphery by a guide mechanism with a guide mechanism shaft being a center of swivel rotation; an elastic member pressing step of pressing the elastic member disposed outer side in a cross direction than the continuum of the elastic member that is disposed in a predetermined wavy shape by the swinging mechanism; a cutting step of cutting the elastic member conveyed by the guiding mechanism between the outside pressing mechanism and the continuum in the cross direction; a joining step of conveying the elastic member and the continuum that are supplied from the guiding mechanism so as to be taken along an outer periphery by a joining mechanism with a joining mechanism shaft being a center of swivel rotation, and conveying a sheet member supplied onto an end portion from the sheet supply mechanism, in the cross direction of the continuum, wherein the continuum is conveyed so that a tangential direction of a deviation point at which the continuum is spaced from the guiding mechanism and a tangential direction of an arrival point at which the continuum reaches the joining mechanism is coincident with each other.

DESCRIPTION OF EMBODIMENTS

Figure 1:
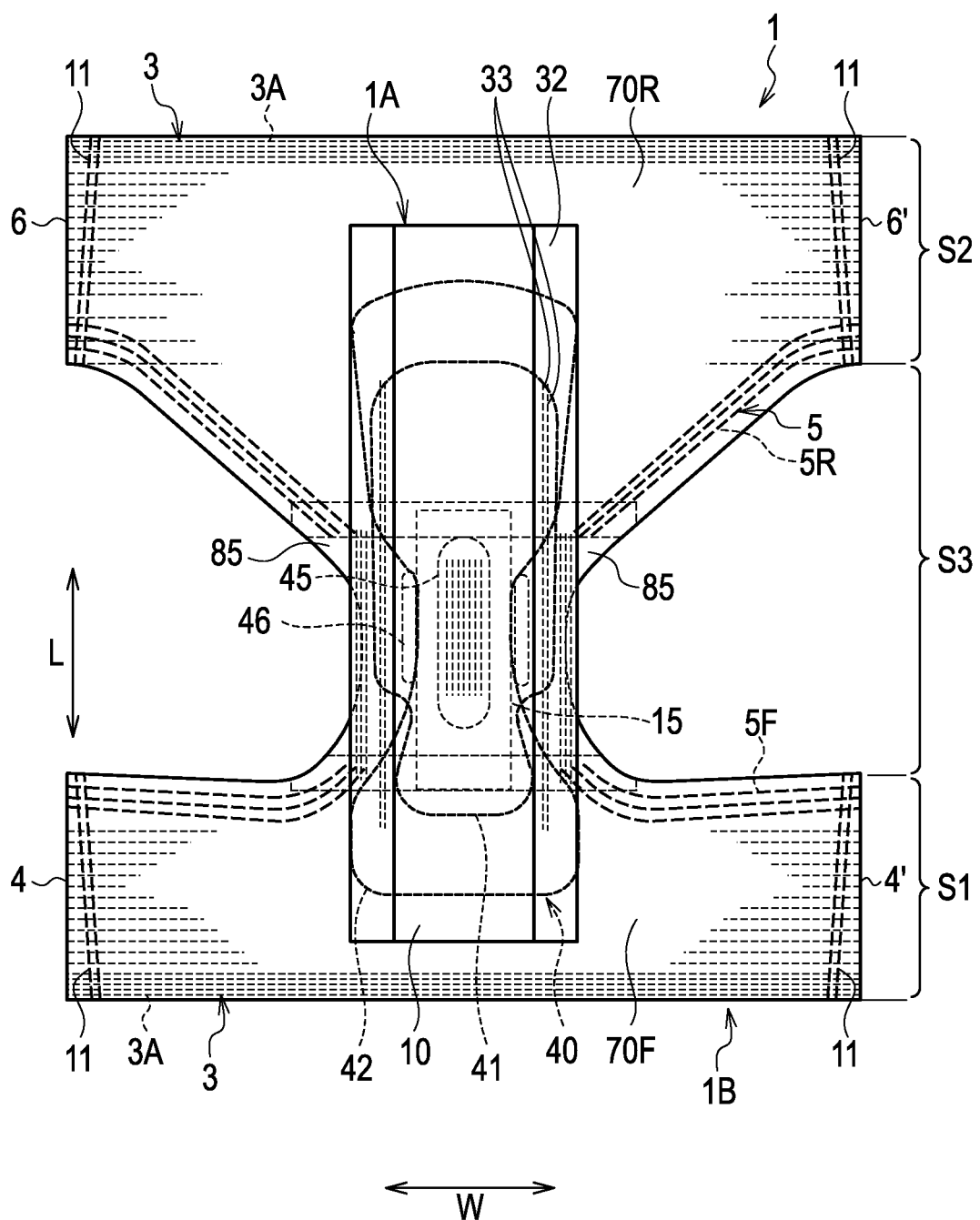
FIG. 1 is an exploded plan view of an absorbent article according to an embodiment.

Hereinafter, an apparatus for manufacturing absorbent articles and a method for manufacturing absorbent articles, according to the present invention, will be described with reference to the drawings. Specifically, a description will be given with respect to: (1) Structure of Absorbent Article; (2) Method for Manufacturing Absorbent Articles; (3) Structure of Apparatus for Manufacturing Absorbent Articles; and (4) Other Embodiments.

In the following description of the drawings, same or similar constituent elements are designated by same or similar reference numerals. However, it is to be kept in mind that the drawings are merely schematic, and rates or the like of the respective dimensions are different from real ones. Therefore, specific dimensions or the like should be determined in consideration of the following description. In addition, it is a matter of course that among the respective drawings as well, portions with different dimensional relationship or rates are included.

(1) Structure of Absorbent Article

First, a structure of an absorbent article 1 according to the embodiment will be described with reference to the drawings. FIG. 1 is an exploded plan view showing a state in which the absorbent article 1 according to the embodiment is exploded. In the embodiment, the absorbent article 1 is a disposable diaper of a pants type. It should be noted that the exploded plan view of FIG. 1 is diagram in which leg-line elastic member and hipline elastic member are in an expanded state such that wrinkles are not formed in an exterior body, for example, that configure the absorbent article 1.

In the embodiment, the pants-type disposable diaper is a diaper formed in advance in the pants type. It is to be noted that in the embodiment, the above disposable diaper is constituted so as to manufacture the disposable diaper of the pants type, whereas the disposable diaper may be constituted so as to manufacture a disposable diaper of an open type. The disposable diaper of the open type is a disposable diaper in which the diaper is opened in a state before use, and predetermined portions of the product are fastened with each other by attachment tape or the like to thereby attach to a user.

The absorbent article 1 has a longitudinal direction L extending to a body foreside and a body backside of a wearer and a widthwise direction W that is orthogonal to the longitudinal direction L.

The absorbent article 1 has a front waistline region S1 corresponding to a front waistline of a wearer, a back waistline region S2 corresponding to a back waistline of the wearer, in a longitudinal direction L of the absorbent article 1, and a crotch region S3 corresponding to a crotch of the wearer and positioned between the front waistline region S1 and the back waistline region S2.

A front waistline edge portion 4 lying outside in one widthwise direction of the absorbent article 1 in the front waistline region S1 is joined with a back waistline edge portion 6 lying outside in one widthwise direction of the back waistline region S2, and a front waistline edge portion 4' lying outside in the other widthwise direction is joined with a back waistline edge portion 6' lying outside in the other widthwise direction, whereby the absorbent article 1 is formed in the pants type. In the front waistline region S1 and the back waistline region S2 of the disposable diaper of the pants type, a joint unit 11 of which the respective edge portion s are joined with each other is formed, and the crotch region S3 is a region inner side than the joint unit 11 in the longitudinal direction.

In the absorbent article 1, a hipline opening unit disposed so as to surround a hip of a wearer and one pair of leg hole opening units disposed so as to surround legs of the wearer are formed in a state in which these opening units are formed in the pants type. A leg hole opening unit is a portion which, in the crotch region S3, is concaved inner side in a widthwise direction than an outside end of a front waistline region in the widthwise direction and an outside end of a back waistline region in the widthwise direction. The periphery of the leg hole opening unit is equivalent to the leg-line portion.

The absorbent article 1 includes: an absorbent main body 1A including a topsheet 10 and an absorber 40 or the like; and an exterior body 1B including a foreside exterior topsheet 70F, a backside exterior topsheet 70R, a foreside exterior backsheet 80F, and a backside exterior backsheet 80R or the like. These constituent elements are joined with each other by an adhesive or thermal fusion deposition, for example.

The exterior body 1B constitutes an exterior portion of the absorbent article 1. The exterior body 1B is disposed at a non-skin contact surface side from the absorbent main body 1A. The foreside exterior topsheet 70F and the foreside exterior backsheet 80F are disposed across the front waistline region S1 and the crotch region S3. The backside exterior topsheet 70R and the backside exterior backsheet 80R are disposed across the back waistline region S2 and the crotch region S3. The foreside exterior topsheet 70F and the foreside exterior backsheet 80F and the backside exterior topsheet 70R and the backside exterior backsheet 80R are disposed so as to be spaced in the longitudinal direction, and are coupled to each other by an intermediate exterior sheet 85.

The absorbent main body 1A includes a topsheet 10, a second sheet 15, an absorber back sheet, and a leakage preventing unit, and is disposed on a wearer's side from the exterior body 1B.

The topsheet 10 is a sheet to form a skin contact surface that is capable of directly coming into contact with a skin of a wearer. The topsheet 10 is disposed on the skin contact surface side from an absorber 40. The topsheet 10 is formed of a liquid permeable sheet such as a hydrophilic unwoven cloth or fiber, an opening plastic film, an opening hydrophobic unwoven cloth.

A second sheet 15 is joined with a non-skin contact surface side of the topsheet 10. The second sheet 15 is disposed between the topsheet 10 and the absorber 40.

The absorber 40 is disposed between a composite sheet on which the topsheet 10 and the second sheet 15 are joined with each other and an absorbent backsheet (not shown). The absorber 40 is disposed at least at a center in a widthwise direction of the crotch region S3. The absorber 40 is formed of mixture powder such as a powdered pulp or a highly absorbent polymer. The absorber 40 is configured by a first absorption layer 41 lying on the non-skin contact surface side of the wearer and a second absorption layer 42 overlapped on the first absorption layer 41 and lying on the skin contact surface side of the wearer.

In the first absorption layer 41, a central slit 45 and a side slit 46, both of which extend in the longitudinal direction, are formed. The side slit 46 is formed outer side in the widthwise direction than the central slit 45. The absorber 40 is constituted so as to be deformed due to the central slit or side slit formed in the absorber 40, when the absorbent article 1 is worn.

The leakage preventing unit has a leakage preventing side sheet 32 and a leakage preventing elastic member 33, and is disposed along the longitudinal direction at widthwise end portions of the absorber 40. The leakage preventing side sheet 32 is provided so as to integrally envelope the topsheet 10 and the absorber backsheet at both side ends in the widthwise direction W of the absorber 40. The leakage preventing side sheet 32 is formed of a sheet such as a liquid impermeable unwoven cloth. One end portion in the widthwise direction of the leakage preventing side sheet 32 is joined with the non-skin surface side of the absorber backsheet, and the other end portion in the widthwise direction of the leakage preventing side sheet 32 is folded back from the lateral side in the widthwise direction of the absorber 40, and is joined with the skin contact surface of the topsheet 10.

The leakage preventing side sheet 32 is joined with a topsheet or the like by a hot melt adhesive. The leakage preventing elastic member 33 is adhered in an expanded state between the absorber backsheet and the leakage preventing side sheet 32. The leakage preventing elastic member 33 respectively contracts in the longitudinal direction both end portions in the widthwise direction of the absorber.

In the front waistline region S1 and the back waistline region S2, a waist gather 3 is provided. The waist gather 3 has an elongated hipline elastic member 3A such as a synthetic rubber arranged so as to expand and contract along the widthwise direction W. The waist gather 3 is continuous from one front waistline edge portion 4 lying outside in the widthwise direction W of the absorbent article 1 in the front waistline edge portion 4 up to the other front waistline edge portion 4' and is continuous from one back waistline edge portion 6 lying outside in the widthwise direction W of the absorbent article 1 in the back waistline region S2 up to the back waistline edge portion 6'.

At the periphery of the leg hole opening unit, a leg gather 5 is provided. At least a part of the leg gather 5 is disposed along the leg hole opening unit. The leg gather 5 is formed of a front leg-line elastic member 5F disposed in the front waistline region S1 and a back leg-line elastic member 5R disposed across the back leg-waistline region S2 and the crotch region S3.

The front leg-line elastic member 5F and the hipline elastic member 3A are disposed between the foreside exterior topsheet 70F and the foreside exterior backsheet 80F, and the back leg-line elastic member 5R and the hipline elastic member 3A are disposed between the backside exterior topsheet 70R and the backside exterior backsheet 80R. The steps of disposing the hipline elastic member 3A, the front leg-line elastic member 5F, and the back leg-line elastic member 5R will be described later in detail.

(2) Method for Manufacturing Absorbent Articles

Figure 2:
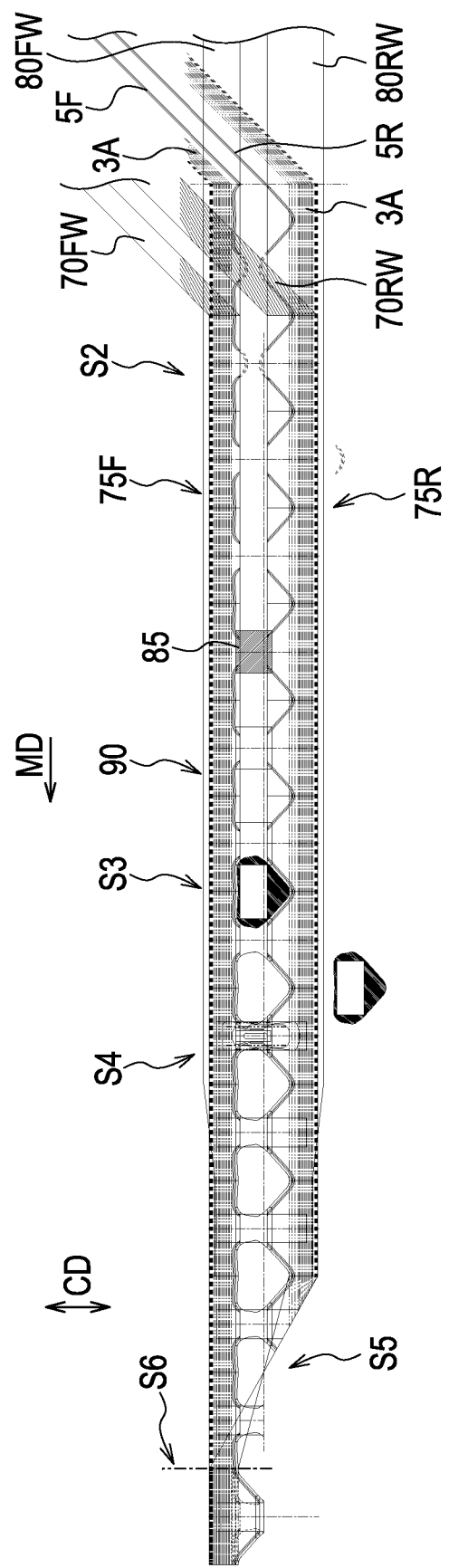
FIG. 2 is a view for explaining the steps of manufacturing absorbent articles according to an embodiment.

Next, one example of a method for manufacturing absorbent articles, according to the embodiment, will be described with reference to FIG. 2. FIG. 2 is a view for explaining the method for manufacturing absorbent articles, and shows a part of a course in which absorbent articles are manufactured. FIG. 2 shows a direction of conveying constituent elements in the course of manufacture as a conveyance direction MD, and shows a direction perpendicular to the conveyance direction as a cross direction CD. The method for manufacturing absorbent articles is to manufacture the absorbent articles 1 in a state in which the articles are continuous in the widthwise direction.

It is to be noted that in respect of a method that is not described in the embodiment, an existing method can be employed. In addition, the manufacturing method described hereinafter is provided as a mere example, and manufacturing by another manufacturing method is also possible.

The method for manufacturing absorbent articles includes at least an absorbent main body forming step S1, an exterior body forming step S2, a leg-line forming step S3, a constituent element joining step S4, a folding step S5, a joining step S6, and a cutting step S7.

In the absorbent main body forming step S1, an absorbent main body 1A is formed. Specifically, for example, an absorption material is laminated to thereby mold an absorber 40, the absorber 40 is disposed on a continuous web constituting a topsheet 10, or a leakage preventing unit is formed.

The exterior body forming step S2 is constituted so that an exterior body 1B is formed. In the embodiment, this step is constituted so that a foreside continuum 75F in which an exterior sheet disposed at an belly-side of a wearer is continuous and a backside continuum 75R in which an exterior sheet disposed at a backside of the wearer is continuous are separately formed, and the foreside continuum 75F and the backside continuum 75R are coupled to each other via an intermediate exterior sheet so as to manufacture an exterior body 1B.

The method for manufacturing absorbent articles includes: an elastic member disposing step of feeding an elastic member while swinging the elastic member along a cross direction crossing a conveyance direction of a sheet-shaped continuum constituting an absorbent article; a guiding step of conveying the elastic member and the continuum so as to be taken along an outer periphery of a guiding mechanism by the guiding mechanism to rotate a guiding mechanism shaft around a center of swivel rotation; an elastic member pressing step of pressing, by an outside pressing mechanism, an elastic member disposed outside in a cross direction more significantly than the continuum among elastic members disposed in a predetermined wavy shape; a cutting step of cutting an elastic member to be conveyed by the guiding mechanism between the outside pressing mechanism and the continuum; and a joining step of conveying the elastic member and the continuum to be supplied from the guiding mechanism so as to be taken along an outer periphery by a joining mechanism to rotate a joining mechanism shaft around a center of swivel rotation, and conveying a sheet member to be supplied from a sheet supply mechanism in a state in which the sheet member is disposed on an end portion in a cross direction of the continuum.

Specifically, between a web constituting the a foreside exterior topsheet 70F and a web constituting a foreside exterior backsheet 80F, a hipline elastic member 3A and a front leg-line elastic member 5F are disposed to thereby form a foreside continuum 75F, and between a web constituting a backside exterior topsheet 70R and a web constituting a backside exterior backsheet 80R, an hipline elastic member 3A and a back leg-line elastic member 5R are disposed to thereby form a backside continuum 75R.

Next, after an unnecessary portion of a front leg-line elastic member 5F and a back leg-line elastic member 5R (a portion deviating from the foreside continuum 75F and the backside continuum 75R) has been cut; the foreside continuum 75F and the backside continuum 75R are joined with each other by the intermediate exterior sheet 85. In this manner, an exterior continuum 90 in which exterior bodies 1B of individual products are continuous in the widthwise direction is formed.

The leg-line forming step S3 is to cut the exterior body 1B along a leg hole opening unit. In this manner, a leg hole opening unit disposed on a leg of a wearer is formed.

The constituent element joining step S4 is to join the exterior body 1B and the absorbent main body 1A. Specifically, the absorbent main body 1A is disposed on a continuum of the exterior body 1B in which a leg hole opening unit is formed, and the absorbent main body 1A and the exterior body 1B are joined with each other via an adhesive.

In the folding step S5, the continuum of the absorbent article in which the absorbent main body 1A and the exterior body 1B are joined with each other is folded with reference to a fold including a center in a cross direction and taken along a conveyance direction.

In the joining step S6, end portions in a widthwise direction of the folded absorbent article are joined with each other. Specifically, a front waistline edge portion 4 and a back waistline edge portion 6 are joined with each other, and a front waistline edge portion 4' and a back waistline edge portion 6' are joined with each other.

In the cutting step S7, the continuum of the absorbent article is cut in size of one product along a longitudinal direction (cross direction) of the absorbent article. In this manner, an absorbent article 1 is manufactured.

(3) Structure of Apparatus for Manufacturing Absorbent Articles

Figure 3:
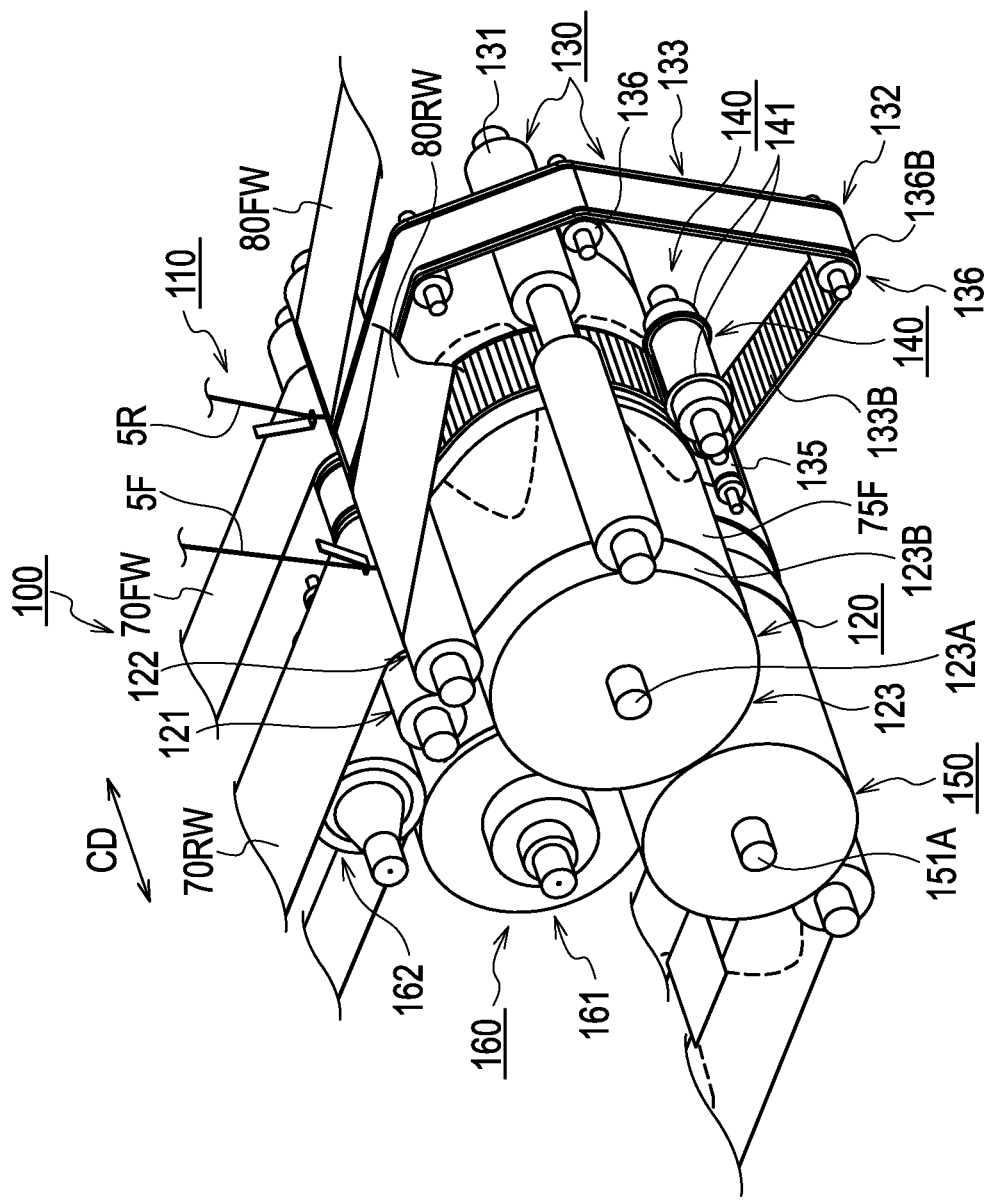
FIG. 3 is a perspective view showing an apparatus for manufacturing absorbent articles, according to an embodiment.
Figure 4:
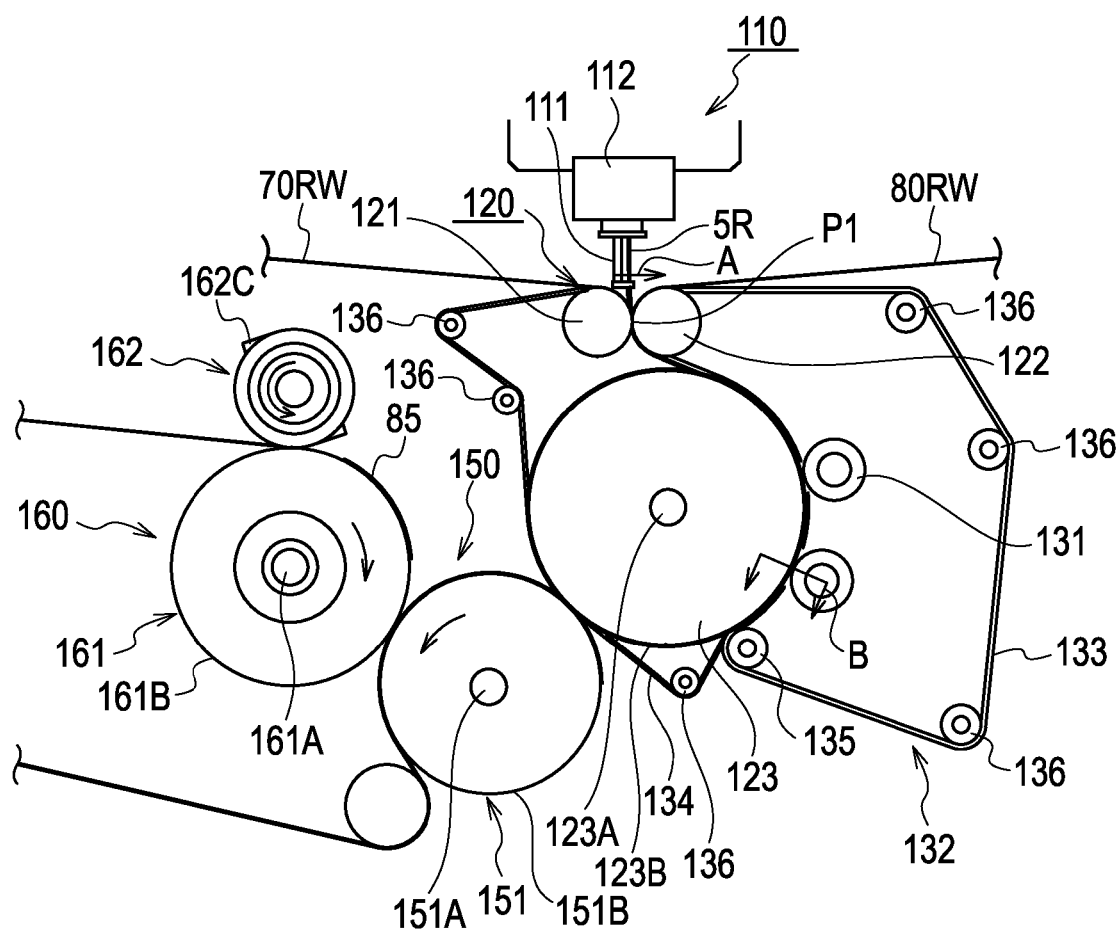
FIG. 4 is a side view showing the apparatus for manufacturing absorbent articles according to an embodiment.

Next, a structure of an apparatus for manufacturing absorbent article for use in the exterior body forming step S2 mentioned above will be described in detail. FIG. 3 is a perspective view schematically showing an absorbent article manufacturing apparatus 100. FIG. 4 is a side view schematically showing the absorbent article manufacturing apparatus 100. The absorbent article manufacturing apparatus 100 is provided with a swinging mechanism 110, a guiding mechanism 120, a pressing mechanism 130, a cutting mechanism 140, a joining mechanism 150, and a sheet supply mechanism 160.

In the embodiment, a foreside mechanism to form an exterior body 1B disposed in a front waistline region S1 disposed at a belly-side of a wearer and a part of a crotch region S3 and a backside mechanism to form an exterior body 1B disposed in a back waistline region S2 disposed at a back-side of the wearer and a part of the crotch region S3 are disposed at both ends in a cross direction.

A foreside continuum 75F and a backside continuum 75R are formed at the same time by the foreside mechanism and the backside mechanism. In addition, the foreside continuum 75F and the backside continuum 75R are joined with each other through an intermediate exterior sheet (sheet member) supplied from a sheet supply mechanism, in the joining mechanism.

The foreside continuum 75F is formed of a foreside exterior topsheet 70F, a foreside exterior backsheet 80F, a hipline elastic member 3A, and a front leg-line elastic member 5F. The backside continuum 75R is formed of a backside exterior topsheet 70R, a backside exterior backsheet 80R, a hipline elastic member 3A, and a back leg-line elastic member 5R.

The foreside mechanism and the backside mechanism pass through an intermediate point between the foreside mechanism and the backside mechanism in a cross direction and is linearly symmetrical around the line taken along a conveyance direction, and their structure are similar. In the following description, one of the foreside mechanism and the backside mechanism will be described, and the other one is not described.

The swinging mechanism 110 is configured by an arm member 111 and a motor 112 (refer to FIG. 4). The arm member 111 guides the front leg-line elastic member 5F and the back leg-line elastic member 5R along the cross direction CD. The swinging mechanism 110 is disposed upward of the guiding mechanism 120 in a state shown in FIG. 4. The motor 112 swings the arm member 111 in the cross direction CD. The swinging mechanism 110 feeds the front leg-line elastic member 5F and the back leg-line elastic member 5R corresponding to a leg of a wearer while swinging these members (reciprocally) along the cross direction CD.

Figure 5:
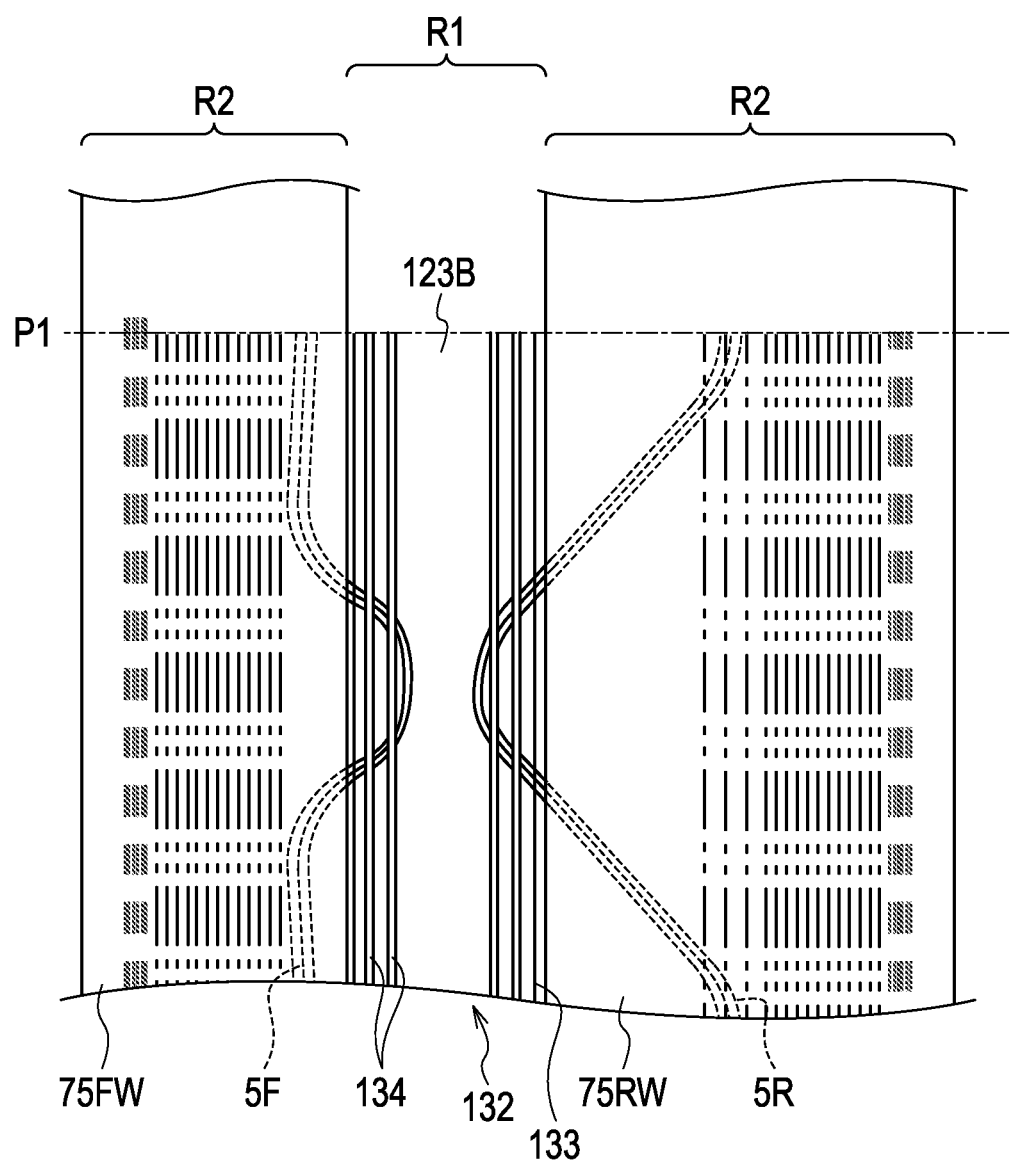
FIG. 5 is a view showing a conveyance state of a continuum in a view indicated by an A arrow shown in FIG. 4.

In the foreside mechanism, a web 70FW constituting the foreside exterior topsheet 70F is conveyed toward downward of the swinging mechanism 110 from the left side shown in FIG. 4, and a web 80FW constituting the foreside exterior backsheet 80F is conveyed toward downward of the swinging mechanism 110 from the right side shown in FIG. 4. At this time, to the web 70FW constitutes the foreside exterior topsheet 70F and the web 80FW constituting the foreside exterior backsheet 80F, an adhesive is applied by an adhesive applying mechanism which is not shown. The swinging mechanism 110 supplies an expanded front leg-line elastic member 5F to a joint point P1 (refer to FIG. 4 and FIG. 5) at which the web 70FW constituting the foreside exterior topsheet 70F and the web 80FW constituting the foreside exterior backsheet 80F join with each other.

The swinging mechanism 110 forms the front leg-line elastic member 5F in a wavy shape having predetermined amplitude. The front leg-line elastic member 5F is disposed in an expanded state between the web constituting the foreside exterior topsheet and the web constituting the foreside exterior backsheet and is disposed in a region protruding outer side in a cross direction (outside in a cross direction oriented to the backside mechanism side) than these webs.

In the backside mechanism, the web 70RW constituting the backside exterior topsheet 70R is conveyed toward downward of the swinging mechanism 110 from the left side shown in FIG. 4, and the web 80RW constituting the backside exterior backsheet 80R is conveyed toward downward of the swinging mechanism 110 from the right side shown in FIG. 4. At this time, in the web 70RW constitutes the backside exterior topsheet 70R and the web 80RW constituting the backside exterior backsheet 80R, an adhesive is applied by an adhesive applying mechanism which is not shown. The swinging mechanism 110 supplies an expanded back leg-line elastic member 5R at a joint point P1 at which the web 70RW constituting the backside exterior topsheet 70R and the web 80RW constituting the backside exterior backsheet 80R join with each other.

The swinging mechanism 110 forms the back leg-line elastic member 5R in a wavy shape having predetermined amplitude. The back leg-line elastic member 5R is disposed in an expanded state between the web constituting the backside exterior topsheet and the web constituting the backside exterior backsheet and is disposed a region protruding outer side in a cross direction (outside in a cross direction oriented to the foreside mechanism side) than these webs.

Herein the wavy shape having the predetermined amplitude denotes a shape in which a distance taken along the conveyance direction MD of one pair of leg-line elastic members varies in a predetermined cycle (for example, in a cycle of product size) with respect to the cross direction CD. It is to be noted that the shape does not always need to be wavy, and may be a zigzag shape.

In addition, a hipline elastic member 3A is disposed in an expanded state on a web constituting an exterior body by an elastic member supply mechanism which is not shown, in the step in which a leg-line elastic member is disposed in a web constituting an exterior body by the swinging mechanism 110. The step of disposing the hipline elastic member is not described.

The guiding mechanism 120 is constituted so as to convey the foreside continuum 75F and the backside continuum 75R so as to be taken along an outer periphery of the guiding mechanism with a guiding mechanism shaft being a center of swivel rotation. The guiding mechanism 120 has a first nip roll 121, a second nip roll 122, and a guide roll 123.

The first nip roll 121 and the second nip roll 122 are nip rolls in which their respective outer periphery are disposed so as to be opposed to each other. The first nip roll 121 conveys the web 70FW constituting the foreside exterior topsheet 70F (or the web 70RW constituting the backside exterior topsheet 70R) along the outer periphery of the first nip roll 121. The second nip roll 122 conveys the web 80FW constituting the foreside exterior backsheet 80F (or the web 80RW constituting the backside exterior backsheet 80R) along the outer periphery of the second nip roll 122.

The first nip roll 121 and the second nip roll 122 causes the web constituting the foreside exterior topsheet 70F (or the web constituting the backside exterior topsheet 70R) and the web constituting the foreside exterior backsheet 80F (or the web constituting the backside exterior backsheet 80R) to abut against each other at the joint point P1, and joins the front leg-line elastic member 5F (or the back leg-line elastic member 5R) between the webs.

The web 70FW constituting the foreside exterior topsheet 70F (or the web 70RW constituting the backside exterior topsheet 70R), the web constituting the foreside exterior backsheet 80F (or the web constituting the backside exterior backsheet 80R), and the leg-line elastic members are spaced from the first nip roll 121 on a downstream side in the conveyance direction than the joint point P1, and are conveyed toward the guide roll 123 along the outer periphery of the second nip roll 122.

Thus, the leg-line elastic member is sandwiched by one pair of nip rolls, whereby the leg-line elastic member is brought into intimate contact with a web at a joint point and then is swung by a swinging member, and in that state, the shape of the leg-line elastic member is easily maintained. Further, while the nip rolls rotate at an angle of 90 degrees, the web in a state in which the leg-line elastic member is sandwiched there between is conveyed so as to be loaded on the outer periphery of the nip roll and thus the shape of the elastic member can be securely adhered onto the web.

For example, if the web and the elastic member are conveyed in a state in which an elastic member supplied from a swinging member and disposed on a web is not securely adhered, the position of the elastic member may be shifted and then the shape may be deformed. Meanwhile, the elastic member sandwiched between the webs is pressed by the nip rolls, and in that state, the elastic member are loaded on the outer periphery of the nip roll and then the loaded elastic member is conveyed and thus the elastic member is securely adhered onto the webs, and a positional shift of the elastic member can be restrained.

The guide roll 123 is disposed on the downstream side of the conveyance direction MD than one pair of nip rolls 121, 122. The guide roll 123 rotates with a rotary shaft (guide mechanism shaft) 123A being a center of swivel rotation to thereby convey the continuums (the foreside continuum and the backside continuum) that are disposed on the outer periphery 123B of the guide roll 123.

The pressing mechanism 130 presses the continuums conveyed by the guide roll 123 toward an outer periphery 123B of the guide roll 123. The pressing mechanism 130 is formed of an inside pressing mechanism 131 and an outside pressing mechanism 132. The inside pressing mechanism 131 presses the continuum (the web and the leg-line elastic member and the hipline elastic member that are disposed on the web). The outside pressing mechanism 132 presses the leg-line elastic member outside of each continuum (deviating from the outside of the continuum).

The inside pressing mechanism 131 is a rotary body disposed so as to be opposed to the outer periphery 123B of the guide roll 123. The inside pressing mechanism 131 presses the continuum in which the leg-line elastic member is disposed in a predetermined wavy shape by the swinging mechanism 110 toward the outer periphery 123B of the guide roll 123. Namely, the inside pressing mechanism 131 presses the leg-line elastic member on the continuum in a state in which the leg-line elastic member is retained in a predetermined wavy shape.

The inside pressing mechanism 131 presses a second region R2 (refer to FIG. 5) in which the foreside continuum 75F and the backside continuum 75R are disposed. The leg-line elastic member is pressed by the inside pressing mechanism 131 in a region in which the elastic member is disposed on the continuum among the regions formed in a predetermined wavy shape. It is to be noted that in the embodiment, the foreside continuum 75F and the backside continuum 75R are disposed so as to be spaced from each other at intervals from each other in the cross direction and thus the inside pressing mechanism 131 is also disposed so as to be spaced from each other at intervals in the cross direction. Therefore, the inside pressing mechanism 131 is constituted so as to press the outside in the cross direction in the entire manufacturing apparatus 100.

The outside pressing mechanism 132 presses only the leg-line elastic member toward the outer periphery 123B of the guide roll 123. Namely, the outside pressing mechanism 132 presses the leg-line elastic member deviating from the continuum in a state in which the elastic member is retained in a predetermined wavy shape in a first region (refer to FIG. 5) R1 lying between the foreside continuum 75F and the backside continuum 75R. It is to be noted that the first region is a region in which inner side of the cross direction CD than an inside end portion in the cross direction of the continuum. In addition, the first region R1 is a region in which the leg-line elastic member is not adhered to the continuum (in the embodiment, the region for only the leg-line elastic member).

Here, it is preferable that the outside pressing mechanism 132 presses the leg-line elastic member toward the outer periphery 123B of the guide roll 123 at least at two or more pressing points in one wavy shape deviating from the continuum.

The outside pressing mechanism 132 is disposed inner side the cross direction CD than the inside pressing mechanism 131. The outside pressing mechanism 132 is arranged at least along the conveyance direction MD between a joint point P1 which is a nip roll arrival point and the cutting mechanism 140. Namely, the outside pressing mechanism 132 continuously presses the leg-line elastic member lying in the first region R1 until at least the leg-line elastic member is cut.

The outside pressing mechanism 132 is provided with: one pair of flat belts 133 formed in an endless shape; a plurality of round belts 134 formed in an endless shape; a plurality of belt pressing rolls 135; and a plurality of belt guide rolls 136.

Figure 6:
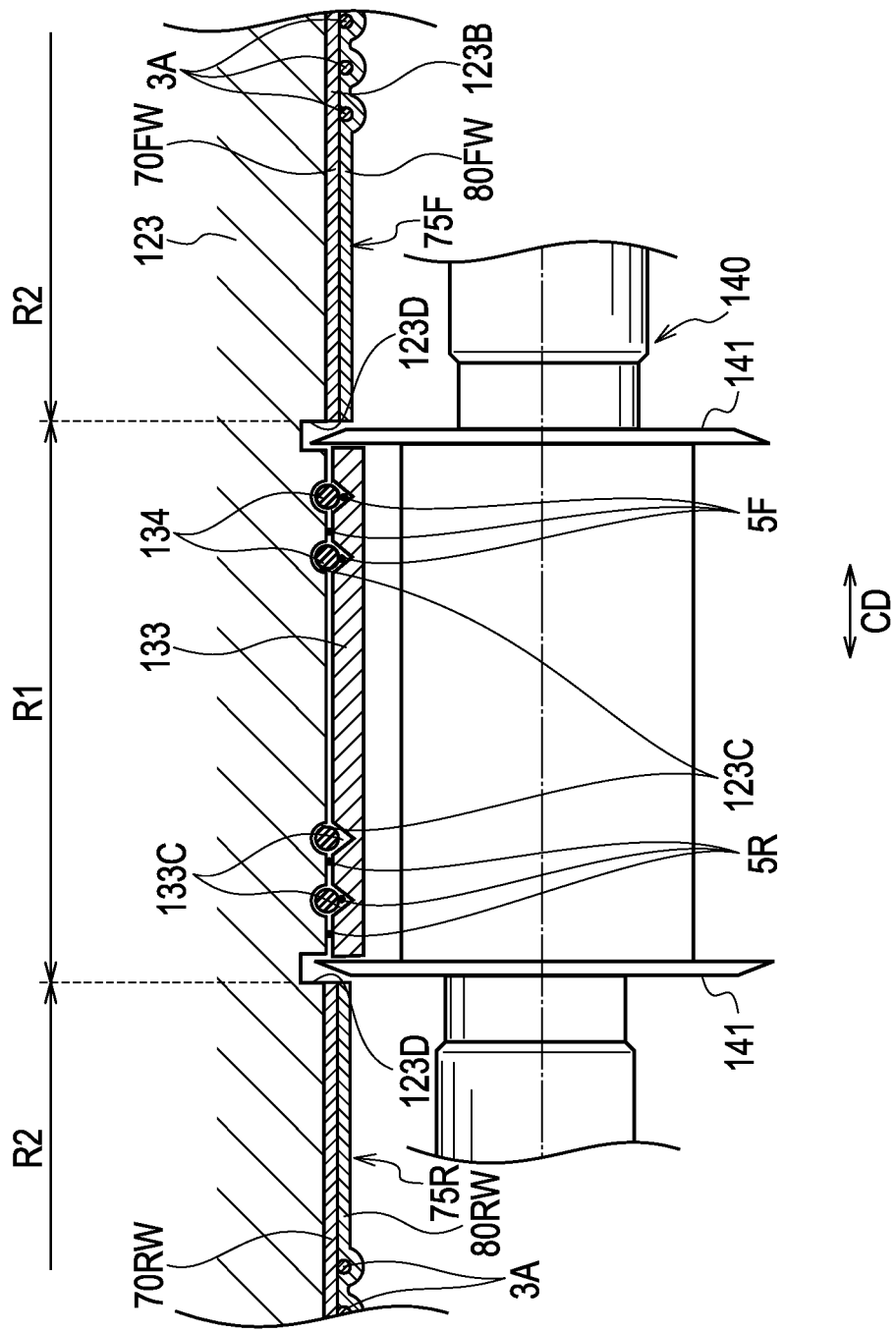
FIG. 6 is a sectional view taken along the line B shown in FIG. 4.

FIG. 6 is a sectional view taken along the line shown in FIG. 4. A flat belt 133 presses one pair of leg-line elastic members deviating from the foreside continuum 75F and the backside continuum 75R toward the outer periphery 123B of the guide roll 123. The flat belt 133 is formed by employing an elastic member (for example, a rubber member).

The flat belt 133 is rotatable along the conveyance direction MD, and has an arc portion forming an arc shape along an outer periphery of the guide roll 123. On a face which does not come into contact the leg-line elastic member of the flat belt 133, a plurality of teeth-shaped convex units 133B are formed so as to be meshed with convex units 136B (refer to FIG. 3) of the guide roll 136 to be described later. The convex units 133B are disposed in the conveyance direction MD at predetermined intervals. A so called flat belt 133 is configured by a timing belt (toothed belt).

On a surface of a flat belt 133 opposed to a round belt 134 (that is, a face coming into contact with a leg-line elastic member), a concave unit 133C with which at least a part of the round belt 134 engages is formed via the leg-line elastic member. Namely, a part of the leg-line elastic member and a part of the round belt 134 cut into the concave unit 133C. The concave unit 133C is provided so as to be continuous along a rotational direction of the flat belt 133. A depth of the concave unit 133C is smaller than a height of the round belt 134 taken along a depth direction of the concave unit 133C, that is, a thickness of the round belt 134.

The round belt 134 is arranged between the guide roll 123 and the flat belt 133. The front leg-line elastic member 5F and the back leg-line elastic member 5R are held by the round belt 134 and the flat belts 133. Two round belts 134 are provided on the front leg-line elastic member 5F side and the back leg-line elastic member 5R side. The round belt is made of an elastic member (for example, a rubber member).

A thickness of the round belt 134 is smaller than a length (width) taken along the cross direction CD of the flat belt 133. A sectional shape taken along in a lateral direction of the round belt 134 is circular. The round belt 134 cuts into the concave unit 133C together with a part of the leg-line elastic member to thereby press the leg-line elastic member.

Here, on the outer periphery of the guide roll 123, a concave unit 123C (drum side concave unit) into which at least part of the round belt 134 cuts is formed. The concave unit 123C is provided so as to be continuous along a rotational direction of the guide roll 123. A depth of the concave unit 123C is smaller than a height of the round belt 134 taken along a depth direction of the concave unit 123C, that is, a thickness of the round belt 134.

A belt pressing roll 135 presses the flat belt 133 and the round belt 134 toward the outer periphery of the guide roll 123. The belt pressing roll 135 is arranged inner side than the inside pressing mechanism 131 in the cross direction CD.

On an outer periphery of the belt pressing roll 135, a tooth-shaped convex unit (not shown) is formed so as to be meshed with the convex units 133B of the flat belt 133. The convex units are disposed at predetermined intervals in a rotational direction of the belt pressing roll 135.

It is to be noted that among a plurality of belt pressing rolls 135, at least one belt pressing roll 135 may be a roll mechanism that is capable of adjusting strength of pressing the flat belt 133 and the round belt 134 against the outer periphery of the guide roll 123.

A belt guide roll 136 guides swivel rotations of the flat belt 133 and the round belt 134. The belt guide roll 136 is provided in plurality on a swivel passageway of the flat belt 133 and on a swivel passageway of the round belt. On an outer periphery of the belt guide roll 136, a gear-shaped convex unit (not shown) so as to be meshed with a convex unit 133B of the flat belt 133 or a concave unit (not shown) into which at least part of the round belt 134 is inserted are formed. It is to be noted that among a plurality of belt guide rolls 136, at least one belt guide roll 136 may be a roll mechanism that is capable of adjusting a tension of the flat belt 133 or the round belt.

A cutting mechanism 140 cuts a leg-line elastic member which deviates to the outside of a continuum, and the elastic member is pressed by the outside pressing mechanism 132. The cutting mechanism 140 is arranged on a downstream side in the conveyance direction MD than the inside pressing mechanism 131.

The cutting mechanism 140 has a cutter roll 141 to cut a leg-line elastic member. The cutter roll 141 is a disk-shaped that is rotatable along the conveyance direction MD, and blades are formed on an outer periphery of the cutter roll. The cutter roll 141 performs cutting in abutment against the leg-line elastic member.

Of the outer periphery 123B of the guide roll 123, at a portion opposed to the cutter roll 141, a concave unit 123D into which the cutter roll is inserted is formed (refer to FIG. 6). The concave unit 123D is concaved inside in a radial direction more significantly than an outer periphery against which a web abuts. An outer circumferential end of the cutter roll 141 advances into the concave unit 123D, and lies inside in a radial direction more significantly than an outer periphery 123B of the guide roll 123. A leg-line elastic member is cut by the outer circumferential end of this cutter roll 141.

It is to be noted that the cutting mechanism is not limitative to a structure of the embodiment, and is constituted to have an upper blade or a lower blade that is a rotary body disposed to be opposed to each other so that a circumferential edge that is a part of the upper blade unit overlaps on a circumferential edge that is a part of the lower blade so as to be thereby sandwich and cut a leg-line elastic member.

In a mechanism provided with an upper blade and a lower blade, however, it is considered that surfaces of the upper blade and the lower blade are worn due to a contact between the upper blade and the lower blade, requiring maintenance. However, as in the embodiment, this mechanism is configured only by a cutter roll, whereby cumbersomeness of maintenance can be reduced.

An outer circumferential end of the cutter roll is arranged inner side in a cross direction than a second region R2 that is pressed by the inside pressing mechanism 131. In the embodiment, as shown in FIG. 6, the cutter roll is arranged between an inside end portion in a cross direction of the foreside continuum 75F (or backside continuum 75R) and an outside end portion in a cross direction of the outside pressing mechanism 132. In this manner, a leg-line elastic member deviating from a continuum is cut.

The outside pressing mechanism is provided in this way, whereby the leg-line elastic member can be cut while the elastic member is pressed by the outside pressing mechanism. The leg-line elastic member is cut in an expanded state by being pressed by the outside pressing mechanism. Therefore, in comparison with a case in which the leg-line elastic member is cut in a contracted state, the leg-line elastic member is easily cut, and a product quality failure can be restrained. Further, if a continuum contracts, a position associate with a sheet member may be shifted. However, a contraction force of the continuum is restrained, whereby a positional shift between the sheet member and the continuum can be restrained.

In addition, a continuum at which a cut elastic member is disposed is conveyed in a state in which the continuum comes into contact with a top of an outer periphery of a guide roll or a joining roll that is to be described later. A slippage of the continuum hardly occurs due to a frictional force between the continuum and the outer periphery of the guide roll or the like, and contraction of the continuum due to a contraction force of the elastic member can be restrained.

Further, a slippage of a continuum on an outer periphery at the time of conveyance can be effectively restrained by enhancing a frictional coefficient on an outer periphery of a guide roll or an outer periphery of a joining roll. For example, as a structure to enhance a frictional coefficient, there can be exemplified a structure to apply a surface treatment such as a silicon coating or a plasma coating or to apply a satin finish together with these surface treatments.

Further, as a structure to restrain contraction at the time of conveyance of a continuum, there is a structure in which a hole-like portion is further formed on an outer periphery and a suction mechanism is provided inside a rotational mechanism and further, the continuum is suctioned by the suction mechanism. With such a structure, a movement of the continuum conveyed along the outer periphery can be restrained.

An elastic member-collection mechanism which is not shown is disposed on a downstream side in a conveyance direction of the cutting mechanism 140. At the downstream side of the cutting mechanism 140, a flat belt is spaced from a guide roll and a round belt. In this manner, a leg-line elastic member cut by the cutting mechanism 140 can be spaced from the guide roll and the round belt. The elastic member-collection mechanism suctions and re-collects the elastic member on the guide roll and the round belt by way of a suction means.

A joining mechanism 150 is disposed on a downstream side in a conveyance direction more significantly than the elastic re-collection mechanism. The joining mechanism (joining mechanism shaft) 150 is provided with a joining roll that rotates with a rotary shaft 151A being a center of swivel rotation and then conveys continuums (foreside continuum and backside continuum) disposed on an outer periphery 151B thereof. A foreside continuum 75F and a backside continuum 75R in which a leg-line elastic member is cut by the cutting mechanism 140 are spaced from the guide roll 123 and then are supplied to a joining roll.

A joining roll 151 is configured by: a first joining roll 152 which has an outer periphery on which an end portion in a cross direction of a continuum and the intermediate exterior sheet 85 are disposed, and which rotates with a rotary shaft being a center of swivel rotation; and second joining roll 153 having an outer periphery on which a region other than the end portion in the cross direction of the continuum is disposed, and which rotates with a rotary shaft being a center of swivel rotation.

In the joining roll of the embodiment, the intermediate exterior sheet 85 is supplied to a central portion in a cross direction of the joining roll, and a foreside continuum 75F and a backside continuum 75R are supplied to both end portions in the cross direction of the joining roll. Therefore, a second joining roll 153 is provided at each end portion in the cross direction of the joining roll, and a first joining roll 152 is provided at a center in a cross direction between the second joining rolls 153. A first joining roll is constituted so that an end portion in a cross direction of a continuum, and a sheet member are disposed so that these constituent elements are joined with each other.

Figure 7:
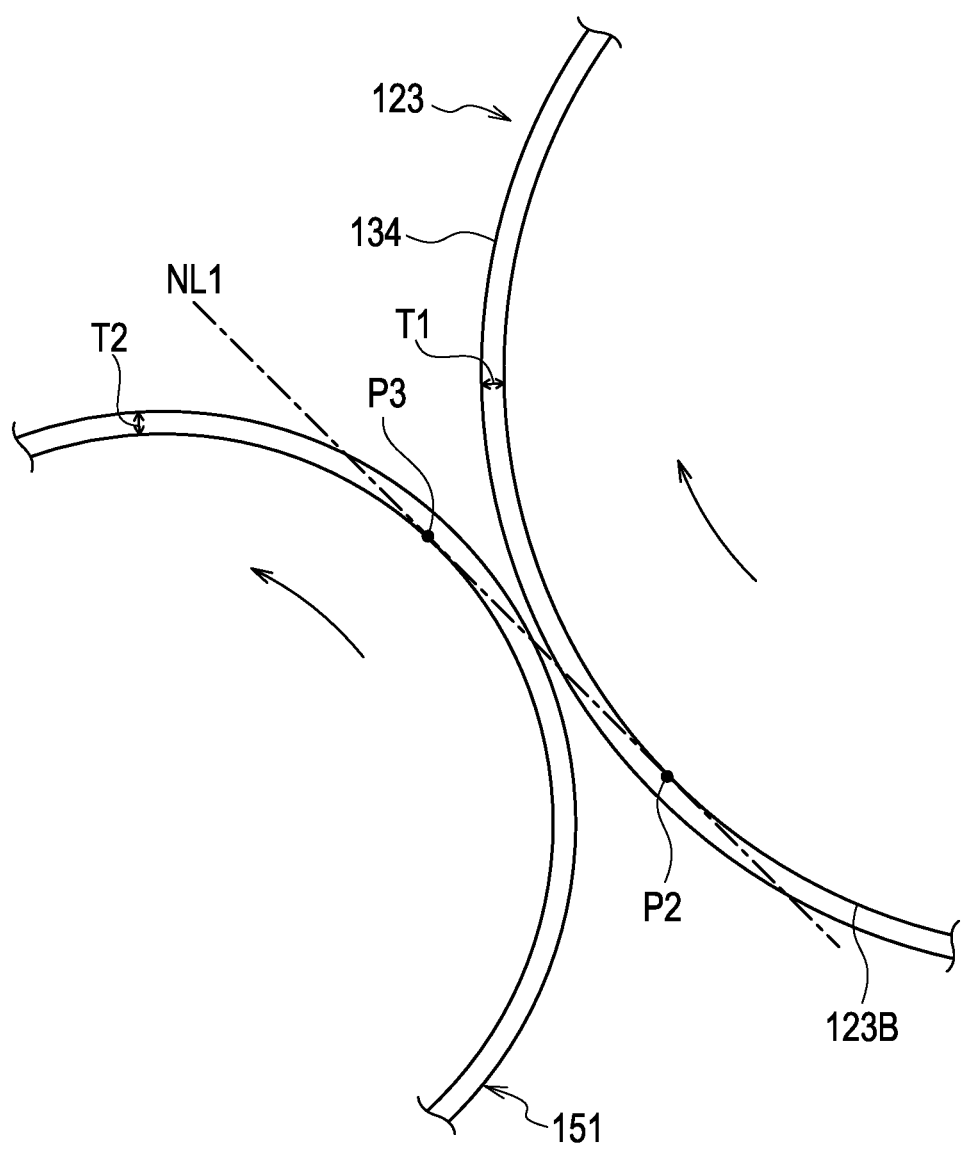
FIG. 7 is an enlarged schematic view of a portion to which a continuum is to be guided from a guide roll to a joining roll.

FIG. 7 is an enlarged view schematically showing a portion at which a continuum is guided from the guide roll 123 to the joining roll 151. The continuum is disposed across a part of the first joining roll and the second joining roll. Reference numeral P2 shown in FIG. 2 indicates a continuum deviation point at which a continuum moving from the guide roll 123 to the joining roll 151 is spaced from the guide roll 123, and reference numeral P3 indicates a continuum arrival point at which a continuum reaches the guide roll. A phantom line NL1 is in a tangential direction at the continuum deviation point P2 and in a tangential direction of the continuum arrival point P3. In the embodiment, the tangential direction at the continuum deviation point P2 and the tangential direction at the continuum arrival point P3 are coincident with each other.

For example, the tangential direction at the continuum deviation point 2 and the tangential direction at the continuum arrival point P3 are displaced from each other, a continuum may be distorted between the continuum deviation point P2 and the continuum arrival point P3. If the continuum is distorted, no constant tensile stress occurs with the continuum, and contraction due to an elastic member may only partly occur. However, since the tangential direction at the continuous deviation point P2 and the tangential direction at the continuum arrival point P3 are coincident with each other, distortion of the continuum can be restrained between deviation from the guide roll 123 and arrival at the joining roll 151, and a partial contraction of the continuum can be restrained.

It is noted that a round belt abuts against a central portion in the cross direction of the guide roll (that is, the round belt abut against a portion between a face with which the foreside continuum 75F comes into contact and a face with which the backside continuum 75R comes into contact). In the round belt, a halve (a thickness for a radius) positioned inside in a radial direction is disposed in a concave unit of the guide roll, whereas a halve (a thickness for a radius) positioned outside in the radial direction protrudes outside in the radial direction more significantly than the outer circumference of the guide roll. This protrusion portion is shown as T1 in FIG. 7. Therefore, between the guide roll and the joining roll, a gap is formed so that the round belt on the guide roll and the outer periphery of the first joining roll of the joining roll do not interfere with each other.

The joining roll 151 conveys the foreside continuum 75F and the backside continuum 75R along the outer periphery on the downstream side in the conveyance direction more significantly than the continuum arrival point P3. Further, on the downstream side in the conveyance direction more significantly than the continuum arrival point P3, the intermediate exterior sheet 85 is supplied from the sheet supply mechanism 160 to the joining roll 151.

The sheet supply mechanism 160 cuts a sheet member constituting the intermediate exterior sheet, and supplies the intermediate exterior sheet 85 to the first joining roll 152 of the joining roll 151. The sheet supply mechanism 160 has: a sheet conveyance roll 161 rotating with a rotary shaft 161A being a center of swivel rotation, and conveying a continuous sheet member along an outer periphery; and a cutter roll 162 disposed so as to be opposed to the sheet conveyance roll 161 and cutting the sheet member conveyed by the sheet conveyance roll in individual product lengths.

In the sheet conveyance roll 161, a suction mechanism (not shown) is disposed inside of an outer periphery 161B, and a sheet member on the outer periphery 161B is suctioned toward the outer periphery 161B.

At an outer circumferential edge of the cutter roll 162, two cutting blades 162C (refer to FIG. 4) are provided so as to be spaced from each other in a circumferential direction. The cutter roll 162 rotates at a constant speed, and cuts a sheet member on the outer periphery every time the cutter roll goes halfway round.

To the sheet conveyance roll, from a sheet supply unit which is not shown, a sheet member is supplied at a lower speed than a movement speed on an outer periphery of the sheet conveyance roll. In s state before the sheet member is cut by the cutter roll 162, the sheet member moves at a supply speed of the sheet member by the sheet supply unit. However, in a state after a sheet member is cut by the cutter roll 162, the intermediate exterior sheet 85 moves at a movement speed of the outer periphery 161B of the sheet conveyance roll.

Figure 8:
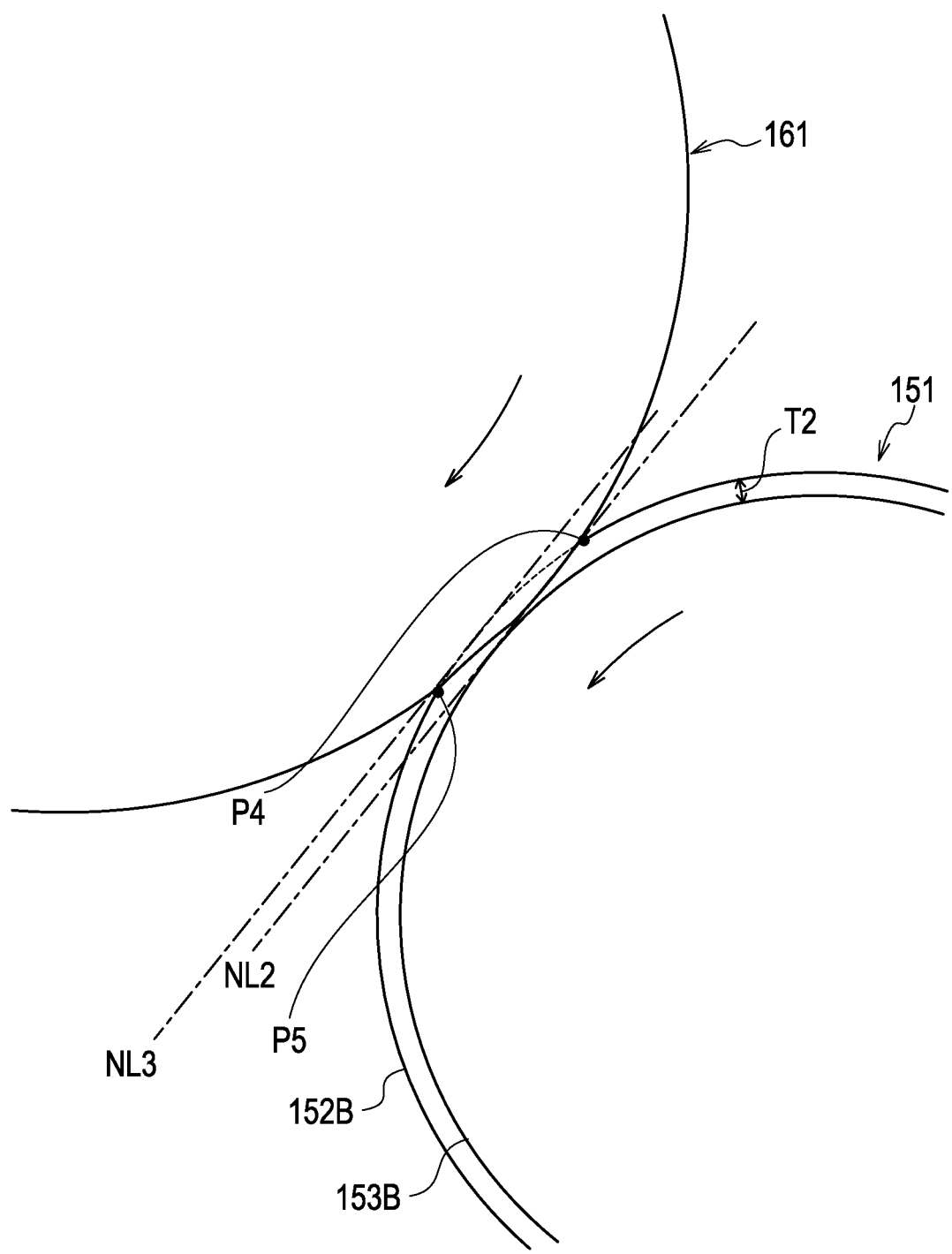
FIG. 8 is an enlarged schematic view of a portion to which a continuum is to be guided from a sheet conveyance roll to a joining roll.

FIG. 8 is an enlarged view schematically showing a portion at which the intermediate exterior sheet 85 is guided from the sheet conveyance roll 161 to the first joining roll 152 in the side view shown in FIG. 4. P4 shown in FIG. 8 is an intermediate sheet abutment point P4 at which the intermediate exterior sheet 85 abuts against the sheet conveyance roll 161, and P5 is an intermediate sheet deviation point P5 at which the first joining roll 152 and the sheet conveyance roll 161 is spaced from each other, and the intermediate exterior sheet 85 is spaced from the sheet conveyance roll 161. A phantom line NL2 is a tangential direction of the sheet conveyance roll 161 at the intermediate sheet abutment point P4, and a phantom line NL3 is a tangential direction of the first joining roll 152 at the intermediate sheet deviation point P5. In the embodiment, the tangential direction at the intermediate sheet abutment point P4 and the tangential direction at the intermediate sheet deviation point P5 are parallel to each other.

For example, if the tangential direction at the intermediate sheet abutment point P4 and the tangential direction at the intermediate sheet deviation point P5 are not parallel to each other, the intermediate exterior sheet 85 may be distorted between the intermediate sheet abutment point P4 and the intermediate sheet deviation point P5. If the intermediate exterior sheet 85 is distorted, a position of the intermediate exterior sheet 85 is shifted, and a positional shift between the intermediate sheet and the continuum may occur. However, since the tangential direction at the intermediate sheet abutment point P4 and the tangential direction at the intermediate sheet deviation point P5 are substantially parallel to each other, an occurrence of distortion of the intermediate exterior sheet 85 can be restrained between deviation from the sheet conveyance roll 161 and arrival at the joining roll 151, and a positional shift of the intermediate exterior sheet can be restrained.

At the intermediate sheet abutment point P4, the intermediate exterior sheet 85 is disposed across an end portion in the cross direction of the foreside continuum 75F and an end portion in the cross direction of the backside continuum 75R. An adhesive is applied in advance to the foreside continuum 75F and the backside continuum 75R or the intermediate exterior sheet 85, an inside end portion in the cross direction of the foreside continuum 75F and an outside end portion in the cross direction of the intermediate exterior sheet 85 are adhered to each other, and an inside end portion in the cross direction of the backside continuum 75R and an outside end portion in the cross direction of the intermediate exterior sheet 85 are adhered to each other.

An elastic member is disposed on an outer periphery of the first joining roll 152. This elastic member on the first joining roll is constituted so as to be deformable in a thickness direction of the intermediate exterior sheet 85 (in a radial direction of the joining roll). The above elastic member is constituted so as to be compressed and deformed between the intermediate sheet abutment point P4 abutting with the sheet conveyance roll 161 and the intermediate sheet deviation point P5 at which the sheet conveyance roll 161 and the first joining roll 152 are spaced from each other. The dotted line on the outer periphery of the first joining roll in FIG. 8 indicates a state before deformation, and from this state, the above elastic member is deformed so as to abut against the outer periphery of the sheet conveyance roll 161.

Thus, the intermediate exterior sheet 85 and the continuum are held by the sheet conveyance roll 161 and the first joining roll 152 between the sheet abutment point P4 and the intermediate sheet deviation point P5, whereby an end portion in the cross direction of the continuum and the intermediate exterior sheet 85 are brought into intimate contact with each other, and the continuum and the intermediate exterior sheet can be rigidly adhered to each other.

It is sufficient if the elastic member is a deformable structure in a radial direction at the time of abutment against the sheet conveyance roll to convey the intermediate exterior sheet, and a material therefor is not limited. For example, an elastic member is made of a silicon rubber, whereby even in the case where adhesive such as a hot melt adhesive comes out, the adhesive can be easily released from an outer periphery, and winding of a sheet member to be conveyed can be prevented.

In addition, a swivel radius of an outer periphery of the first joining roll is greater than a swivel radius of an outer periphery of the second joining roll, and the outer periphery of the first joining roll protrudes to the outside in a radial direction more significantly than the outer periphery of the second joining roll. This protrusion portion is shown as T2 in FIG. 8.

In addition, the joining mechanism is provided with a driving mechanism to rotatably drive only the second joining roll 153 of the first joining roll 152 and the second joining roll 153. Since the swivel radius of the outer periphery of the first joining roll 152 is greater than the swivel radius of the outer periphery of the second joining roll 153, if the first joining roll 152 and the second joining roll 153 rotate with a same rotary shaft being a center of swivel rotation, a speed of the outer periphery of the first joining roll 152 is faster than a speed of the outer periphery of the second joining roll 153.

However, since the intermediate exterior sheet to be conveyed by the outer periphery of the first joining roll and the continuum to be conveyed by the outer periphery of the second joining roll are adhered to, and are integrated with each other, if the speed of the outer periphery of the first joining roll and the speed of the outer periphery of the second joining roll are different from each other, there is an apprehension that a distortion or a twist occurs between the intermediate exterior sheet and the continuum.

Therefore, the joining mechanism according to the embodiment is provided with a driving means (not shown) for driving only the second joining roll. This joining mechanism is constituted so that a driving force by the driving means is not transmitted to the first joining roll, and is also constituted so as not to rotate the first joining roll by the driving means. In this manner, the first joining roll 152 rotates in accordance with the first joining roll via a continuum to be conveyed by the second joining roll 153. In this manner, rotational speeds of the first joining roll and the second joining roll are made different from each other, whereby a distortion or a twist exerted by the same rotational speed can be restrained.

(4) Other Embodiments

As described above, while the contents of the present were disclosed through the embodiment of the present invention, it should not be understood that a discussion and drawings forming a part of this disclosure limit the present invention. From this disclosure, a variety of substitutive embodiments, examples, and operational techniques would have been self-evident to one skilled in the art.

While, in the embodiment, the foreside continuum 75F and the backside continuum 75R are formed separately and then the foreside mechanism and the backside mechanism are provided in one pair in order to couple these continuums to each other by a sheet member, a manufacturing apparatus according to the present invention is not limitative to this structure. For example, all of the swinging mechanism 110, the guiding mechanism 120, the pressing mechanism 130, the cutting mechanism 140, the joining mechanism 150, the sheet supply mechanism 160, the sheet supply mechanism, and the rubber re-collecting mechanism are provided on one by one basis, an elastic member is disposed at one continuum, and a sheet member may be constituted so as to join with only the single continuum.

In addition, while, in the embodiment, an elastic member is disposed in a wavy shape at a respective one of the foreside continuum 75F and the backside continuum 75R, and is constituted so as to join a sheet member after the elastic member has been cut, it is possible to apply to manufacture of a variety of continuums without being limitative to this structure.

For example, in the manufacturing steps of manufacturing absorbent articles in a continuous state in a longitudinal direction of the absorbent articles, a left leg-line elastic member and a right leg-line elastic member are respectively disposed in a wavy shape at both end portions in a cross direction of a web to be conveyed in a continuous state in the longitudinal direction, and thereafter, an elastic member coming out from the web is cut, and a sheet-shaped member may be bonded at each end portion in the cross direction of the web.

Further, while, in the embodiment, the tangential direction at the intermediate sheet abutment point P4 and the tangential direction at the intermediate sheet deviation point P5 are constituted so as to be substantially parallel to each other, the present invention is not limitative to this structure, and the tangential direction at the intermediate sheet abutment point P4 and the tangential direction at the intermediate sheet deviation point P5 may be constituted so as to cross each other.

Thus, it is a matter of course that the present invention includes a variety of embodiments or the like that are not described herein. Therefore, a technical scope of the present invention is defined by only the specific matters of the invention associated with the scope of claims reasonable from the foregoing description.

The entire contents of Japanese Patent Application No. 2012-124892 (filed on May 31, 2012) is incorporated in the present specification by reference.

INDUSTRIAL APPLICABILITY

It is possible to provide an apparatus for manufacturing absorbent articles and a method for manufacturing absorbent articles, which are capable of disposing an elastic member in an entire region of a leg-line portion while restraining a positional shift between the constituent members.

The invention claimed is:

1. A method for manufacturing absorbent articles, comprising:
   an elastic member disposition step of feeding an elastic member with the elastic member being swung along a cross direction crossing a conveyance direction of a sheet-shaped continuum constituting an absorbent article, and disposing a part of the elastic member on the continuum to which an adhesive is applied;
   a guiding step of conveying the elastic member and the continuum so as to be taken along an outer periphery by a guide mechanism with a guide mechanism shaft being a center of swivel rotation;
   an elastic member pressing step of pressing the elastic member disposed outer side in a cross direction than the continuum of the elastic member that is disposed in a predetermined wavy shape by a swinging mechanism;
   a cutting step of cutting the elastic member conveyed by the guiding mechanism between an outside pressing mechanism and the continuum in the cross direction;
   a joining step of conveying the elastic member and the continuum that are supplied from the guiding mechanism so as to be taken along an outer periphery by a joining mechanism with a joining mechanism shaft being the center of swivel rotation, and conveying a sheet member supplied onto an end portion of the continuum from a sheet supply mechanism, in the cross direction of the continuum,
   wherein
   the joining mechanism has:
      a first joining roll having an outer periphery on which an end portion in the cross direction of the continuum and the sheet member are disposed, and rotating with the joining mechanism shaft being the center of swivel rotation; and
      a second joining roll having an outer periphery on which a region other than the end portion in the cross direction of the continuum is disposed, and rotating with the joining mechanism shaft being the center of swivel rotation,
   the outer periphery of the first joining roll is made of an elastic member,
   the continuum is conveyed so that a tangential direction of a deviation point at which the continuum is spaced from the guiding mechanism and a tangential direction of an arrival point at which the continuum reaches the joining mechanism is coincident with each other,
   a radius of swivel rotation of the outer periphery of the first joining roll is greater than a radius of swivel rotation of the outer periphery of the second joining roll, and
   the joining mechanism comprises a driving mechanism that rotationally drives only the second joining roll of the first joining roll and the second joining roll so that rotational speeds of the first joining roll and the second joining roll are different from each other.

2. The method according to claim 1, wherein
the sheet supply mechanism supplies a sheet onto the end portion of the continuum, in the cross direction of the continuum on a side on which the elastic member is cut, of end portions in the cross direction of the continuum conveyed by the joining mechanism.

3. The method according to claim 1, wherein
the absorbent article comprises a front waistline region configured to be disposed on a belly-side of a wearer, a back waistline region configured to be disposed on a back-side of the wearer, and a crotch region disposed between the front waistline region and the back waistline region,
the elastic member disposition step, the guiding step, the elastic member pressing step and the cutting step are performed in a foreside mechanism processing a foreside continuum constituting the front waistline region and in a backside mechanism processing a backside continuum constituting the back waistline region,
the joining mechanism conveys the foreside continuum supplied from the foreside mechanism and the backside continuum supplied from the backside mechanism in a state in which the foreside and backside continuums are spaced from each other in the cross direction, and
the sheet supply mechanism supplies the sheet member across the foreside continuum and the backside continuum.

4. The method according to claim 1, wherein
a tangential direction of a deviation point at which the sheet member is spaced from the sheet supply mechanism and a tangential direction of an arrival point at which the sheet member reaches the joining mechanism are coincident with each other.

* * * * *